US009140678B2

(12) United States Patent
Soccol et al.

(10) Patent No.: US 9,140,678 B2
(45) Date of Patent: Sep. 22, 2015

(54) INTEGRATED CIRCUIT ARRANGEMENT, DEVICE AND GAS DETECTION METHOD

(71) Applicant: NXP B.V., Eindhoven (NL)

(72) Inventors: Dimitri Soccol, Rotselaar (BE); Youri Victorovitch Ponomarev, Leuven (BE); David van Steenwinckel, Holsbeek (BE)

(73) Assignee: NXP, B.V., Eindhoven (NL)

( * ) Notice: Subject to any disclaimer, the term of this patent is extended or adjusted under 35 U.S.C. 154(b) by 5 days.

(21) Appl. No.: 14/096,147

(22) Filed: Dec. 4, 2013

(65) Prior Publication Data

US 2014/0170762 A1 Jun. 19, 2014

(30) Foreign Application Priority Data

Dec. 14, 2012 (EP) ..................................... 12197186

(51) Int. Cl.
*G01N 33/00* (2006.01)
*G01N 27/02* (2006.01)
*G01N 22/00* (2006.01)

(52) U.S. Cl.
CPC .............. *G01N 33/004* (2013.01); *G01N 22/00* (2013.01); *G01N 27/02* (2013.01); *Y10T 436/20* (2015.01); *Y10T 436/204998* (2015.01)

(58) Field of Classification Search
CPC ................ Y10T 436/00; Y10T 436/10; Y10T 436/204998; Y10T 436/20; G01N 31/005; G01N 31/00; G01N 33/182; G01N 33/00; G01N 21/643; G01N 21/62; G01N 21/00; G01N 27/026; G01N 27/02; G01N 27/00; G01N 22/00; G01N 33/004; G01N 33/0036; G01N 33/027; G01N 33/0009; G01N 33/0004
USPC ........ 436/133, 127, 150, 149; 422/90, 88, 83, 422/50
See application file for complete search history.

(56) References Cited

U.S. PATENT DOCUMENTS

| | | | |
|---|---|---|---|
| 5,376,255 A * | 12/1994 | Gumbrecht et al. .......... | 204/426 |
| 6,166,551 A | 12/2000 | Scott et al. | |
| 2012/0060686 A1 | 3/2012 | Kortunov et al. | |
| 2012/0116683 A1 | 5/2012 | Potyrailo et al. | |
| 2015/0084100 A1 | 3/2015 | Sablong et al. | |

FOREIGN PATENT DOCUMENTS

| | | |
|---|---|---|
| JP | 2004 361335 A | 12/2004 |
| WO | 91/08469 A2 | 6/1991 |

OTHER PUBLICATIONS

Simon, U., et al; "The effect of $NH_3$ on the ionic conductivity of dehydrated zeolites Na beta and H beta"; Microporous and Mesoporous Materials 21; Elsevier Science Publishing, New York, US; pp. 111-116 (Apr. 1, 1998).

Ou, Runqing, et al.; "In-plane impedance spectroscopy of doped polyaniline films"; Journal of Plastic Film and Sheeting, vol. 17, No. 2; Lancaster, PA, US; pp. 184-195 (Apr. 1, 2001).

Virji, Shabnam et al; "Polyailine Nanofiber Gas Sensors: Examination of Response Mechanisms"; Nano Letters, vol. 4, No. 3; pp. 491-496 (Mar. 1, 2004).

Musio, Fernando, et al.; "High-frequency a.c. investigation of conducting polymer gas sensors"; Sensors and Actuators B: Chemical: Int'l J. Devoted to Research and Development of Physical and Chemical Transducers, vol. 23, No. 2/3; Elsevier S.A, Switzerland; pp. 223-226 (Feb. 1, 1995).

Gustafsson, G., et al; "The interaction between ammonia and poly (pyrrole)"; Synthetic Metals, vol. 31, No. 2; Elsevier Sequoia, Lausanne, CH; pp. 163-179 (Aug. 1, 1989 ).

Kaatze, Udo, et al; "Review Article: Broadband dielectric spectrometry of liquids and biosystems"; Measurement Science and Technology, vol. 17, No. 2; IOP, Bristol, GB; pp. R17-R35 (Feb. 1, 2006).

Clarke, Bob; "Chapter 18—Measurement of the dielectric properties of materials at RF and microwave frequencies"; Microwave Measurements—$3^{rd}$ Edition; Institution of Engineering and Technology, London, UK; 52 pages (Jan. 1, 2007).

Endres, H.E.; "Impedance spectroscopy on dielectric gas sensors"; Sensors and Actuators B: Chemical: Int'l J. Devoted to Research and Development of Physical and Chemical Transducters, vol. 22, No. 1; Elsevier S.A. Switzerland; pp. 7-11 (Oct. 1, 1994).

Schroder, C., et al; "On the collective network of ionic liquid/water mixtures. II. Decomposition and interpretation of dielectric spectra"; J. of Chemical Physics, vol. 129, No. 18; 12 pages (Jan. 1, 2008).

Asaki, M.L.T., et al; "Dielectric relaxation and underlying dynamics of acetonitrile and 1-ethyl-3-methylimidazolium triflate mixtures using THz transmission spectroscopy"; J. of Chemical Physics, vol. 116, No. 23; 10 pages (Jan. 1, 2002).

Doan, Tin C.D., et al.; "Carbon dioxide sensing with sulfonated polyaniline"; Sensors and Actuators B: Chemical: Int'l J. Devoted to Research and Development of Physical and Chemical Transducers, vol. 168; Elsevier S.A, Switzerland; pp. 123-130 (Mar. 23, 2012).

Gonzalez-Miquel, Maria, et al; "COSMO-RS Studies: Structure-Property Relationships for $CO_2$ Capture by Reversible Ionic Liquids"; Industrial & Engineering Chemistry Research; vol. 51, No. 49; pp. 16066-16073 (Nov. 30, 2012).

(Continued)

*Primary Examiner* — Christine T Mui

(57) ABSTRACT

An integrated circuit arrangement (100) is disclosed comprising a substrate (210); and a gas such as a $CO_2$ sensor comprising spatially separated electrodes including at least an excitation electrode (132) and a sensing electrode (142); a volume (120) in contact with said pair of electrodes, said volume including a chemical compound for forming a reaction product with said gas in an acid-base reaction; a signal generator (212) conductively coupled to the excitation electrode and adapted to provide the excitation electrode with a microwave signal; and a signal detector (214) conductively coupled to the sensing electrode and adapted to detect a change in said microwave signal caused by a permittivity change in said volume, said permittivity change being caused by said reaction product. A device comprising such an IC arrangement and a method of sensing the presence of a gas using such an IC arrangement are also disclosed.

14 Claims, 6 Drawing Sheets

(56) References Cited

OTHER PUBLICATIONS

Dibenedetto, A., et al; "Hybrid Materials for $CO_2$ Uptake from Simulated Flue Gases: Xerogels Containing Diamines"; Chemsuschem; vol. 1, No. 8-9; pp. 742-745 (Sep. 1, 2008).

Lee, Hsun-Tsing, et al; "Conductivity relaxation of polyaniline"; Makromol. Chem, vol. 194; pp. 2443-2452 (Jan. 1, 1993).

Soares, B.G., et al; "Dielectric behavior of polyaniline synthesized by different techniques"; European Polymer Journal, vol. 42, No. 3; Elsevier, Pergamon Press Ltd, Oxford, GB; pp. 676-686 (Mar. 1, 2006).

Kim, Youngbok, et al; "Broadband Dielectric Spectroscopy CMOS Readout Circuit for Molecular Sensing"; Conference Proceedings of IEEE Int'l Symposium on Circuits and Systems, May 23-26, 2005; Kobe, JP; IEEE Service Center, Piscataway, NJ, US; pp. 5906-5909 (May 23, 2005).

Ikada, Eiji, et al; "Dielectric Properties of Ethanolamines"; Bull. Inst. Chem. Res., Kyoto University; vol. 46, No. 5; pp. 239-247 (Jan. 1, 1968).

Extended European Search Report for application 12197186.5 (Mar. 24, 2014).

Schroder, C., et al; "The influence of polarizability on the dielectric spectrum of the ionic liquid 1-ethyl-3-methylimidazolium triflate"; Phys. Chem. Phys., vol. 13; pp. 12240-12248 (2011).

Shimizu, N., et al; "8-2 Stand-off Gas Sensing System Based on Terahertz Spectroscopy"; Journal of the National Institute of Information and Communication Technology, vol. 55, No. 1; pp. 165-170 (2008).

Griffith, J. R., et al; "NRL Report 6047—Filament-Winding Plastics Part 1—Molecular Structure and Tensile Properties"; U.S. Naval Research Laboratory, Washington, D.C., USA; 22 pages Mar. 16, 1964.

Liu, Yingxin, et al; "Switchable Surfactants"; Science, vol. 313, retreived from the internet www.sciencemag.org; pp. 958-960 (Aug. 18, 2006).

Darwish, Tamin et al.; "Spiropyran-Amidine: A Molecular Canary for Visual Detection of Carbon Dioxide Gas"; Chemistry European Journal, No. 17/41; pp. 11399-11404 (2011).

Heldebrandt, David J., et al; "$CO_2$ binding organic liquids ($CO_2$BOLs) for post-combustion $CO_2$ capture"; Science Direct, Energy Procedia 1, pp. 1187-1195 (2009).

Partial European Search Report for application No. 12197186.5 (Aug. 2, 2013).

\* cited by examiner

INTEGRATED CIRCUIT ARRANGEMENT, DEVICE AND GAS DETECTION METHOD

FIELD OF THE INVENTION

Cross-Reference to Related Applications

This application claims the priority under 35 U.S.C. §119 of European patent application no. 12197186.5, filed on Dec. 14, 2012, the contents of which are incorporated by reference herein.

The present invention relates to an integrated circuit (IC) arrangement comprising a gas sensor.

The present invention further relates to a device including such an IC arrangement.

The present invention yet further relates to a method of detecting a gas using such an IC arrangement.

BACKGROUND OF THE INVENTION

Nowadays, integrated circuits (ICs) may comprise a plethora of sensors, such as gas sensors, relative humidity (RH) sensors, specific analyte detection sensors, and so on. Such sensors may be included in the IC design for a number of reasons.

For instance, a gas sensor may be included in an IC to detect a change in the ambient conditions of a product tagged with the chip such that product quality control can be achieved by monitoring the sensor readings of the chip. This can for instance be used to accurately predict the remaining shelf life of the product, e.g. perishable food stuff. The gas sensor may for instance be adapted to determine changes in the $CO_2$ content of the ambient atmosphere. Alternatively, the gas sensor may be used to detect changes in the gas composition of larger environment such as buildings or may be used in medical application domains, e.g. in breathing apparatuses.

With the on-going diversification of electronic devices or electronic information gathering such as by RF tags on packaged articles, it is often desirable to include different types of sensors in a single IC. For instance, the detection of other environmental parameters, for instance temperature and humidity such as for HVAC (heating, ventilation and air conditioning) control in buildings and cars, are particularly desirable in certain application domains. In addition, sensing of analytes of interest, e.g. $CO_2$, may be desirable in such application domains. However, it is difficult to manufacture $CO_2$ sensors having the desired sensitivity in a cost-effective manner. In particular, impedometric $CO_2$ sensors, i.e. sensors based on measuring the change in the impedance of a material based on its exposure to $CO_2$, suffer from relatively poor sensitivity or at least poor responsiveness.

A potentially interesting approach to $CO_2$ sensing is to use materials that exhibit a change in a physical property upon reacting with $CO_2$. Such materials are known per se. For instance, in NRL Report 6047 "Filament-winding plastics Part 1—Molecular Structure and Tensile Properties" of Mar. 16, 1964 and retrieved from the Internet: https://torpedo.nrl.navy.mil/tu/ps/pdf/pdf_loader?dsn=7590632 on Tuesday 7 Aug. 2012 it is disclosed that m-xylylene diamine and an epoxy resin containing it have a tendency to cloud as the amine absorbs carbon dioxide from the atmosphere.

Moreover, A. Dibenedetto et al. in ChemSusChem, Special Issue: 2nd EuCheMS Chemistry Congress, Volume 1, Issue 8-9, pages 742-745, Sep. 1, 2008 disclose the reversible uptake of $CO_2$ from simulated flue gases by mono- and disilyl amines, either in their free form, as organic (wet) solutions, or as xerogels.

Liu et al. in Science, Vol. 313 (2006) pages 958-960 disclose a surfactant including amidine functional group that can be switched upon exposure to $CO_2$ to a clouded amidinium bicarbonate salt.

Darwish et al. in Chem. Eur. J. 17 (2011), pages 11399-11404 disclose a spiropyran amidine that exhibits a colour change upon formation of the amidinium bicarbonate salt following reaction with $CO_2$.

David J. Heldebrandt et al. in Energy Procedia 1 (2009), pages 1187-1195 disclose a new class of $CO_2$ absorbing materials, referred to as $CO_2$-binding organic liquids ($CO_2$-BOLS) that are neat (solvent-free) liquid mixtures of organic alcohols and organic amidine or guanidine bases, which undergo the following reversible reaction in the presence of $CO_2$:

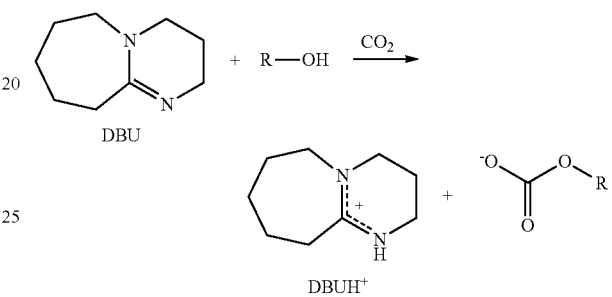

The $CO_2$ may be released by purging the $CO_2$-BOLS e.g. with $N_2$. In the above reaction scheme, DBU (diazabicyclo [5,4,0]undec-7-ene) is shown as the amidinium precursor, although Heldebrandt et al. disclose that a large variety of amidines and guanidines exhibit similar sensitivity to $CO_2$. Similarly, several alkyl alcohols, e.g. hexanol, may be used to form the alkylcarbonate anion. The $CO_2$ uptake was determined using conductivity measurements of the $CO_2$-BOLS dissolved in acetonitrile, as the level of $CO_2$ uptake is (linearly) correlated to the conductivity of the solution. The authors recommend that the absorption capacity of a $CO_2$-BOLS can be increased by choosing a base and alcohol of low molecular weight, e.g. 1,1,3,3-tetramethylguanidine (TMG) and methanol.

The above disclosures have in common that the reversible reaction of the organic compound with $CO_2$ causes a significant change in the charge distribution of the organic compound due to the formation of an ammonium and carboxylate ion pair, which change could potentially be used for sensing purposes, e.g. using transduction principles that could potentially quantify the number of formed ions or ion pairs, as for instance demonstrated in the paper by Heldebrandt et al.

However, exploratory experiments have highlighted that transduction measurements on such ionic liquids are typically restricted to frequencies in the Hz or kHz domain and suffer from a cross-sensitivity to the amount of water present in the sample, which makes this solution less attractive given the cross-sensitivity and the limitations on the speed of the $CO_2$ sensor.

SUMMARY OF THE INVENTION

The present invention seeks to provide an IC arrangement comprising a gas sensor that can be operated at high frequencies.

The present invention further seeks to provide a method for manufacturing such an IC arrangement in a cost-effective manner.

According to an aspect of the present invention, there is provided an integrated circuit arrangement comprising a substrate; and a gas sensor comprising a pair of spatially separated electrodes including an excitation electrode and a sensing electrode; a volume in contact with said pair of electrodes, said volume including a chemical for forming a reaction product with said gas in an acid-base reaction; a signal generator conductively or capacitively coupled to the excitation electrode and adapted to provide the excitation electrode with a microwave signal; and a signal detector conductively or capacitively coupled to the sensing electrode and adapted to detect a change in said high frequency signal caused by a permittivity change in said volume, said permittivity change being caused by said reaction product The present invention is based on the insight that in a microwave alternating electric field, i.e. an electric field of MHz or GHz alternating frequency, a (liquid) medium comprising permanent charges such as associated ion pairs or permanent dipoles formed in an acid-base reaction will exhibit a loss of dielectric permittivity of the reorientation frequency of the permanent charge in the alternating electric field. This principle is for instance utilized in a technique called dielectric (relaxation) spectroscopy, in which the dielectric properties of a medium are measured as a function of frequency. The application of this technique on an IC allows for the detection of dielectric losses at the resonance frequency of the ionic species that are formed by the reaction of the chemical compound with the gas in an acid-base reaction.

In an embodiment, the gas may be $CO_2$, in which the chemical compound acts as the base in the acid-base reaction. In this embodiment, the chemical compound may for instance be an organic compound, and/or may comprise one or more functional groups for reacting with the $CO_2$, such as a diamine, amidine, mono-silyl amine, di-silyl amine or guanidine functional group or combinations thereof. However, it should be understood that other acidic gases, e.g. $SO_2$, or basic gases, e.g. $NH_3$, may be detected in a similar manner using chemical compounds that can react with such gases in an acid-base reaction. Such acid-base reactions and suitable chemical compounds are well-known per se.

In an embodiment, the electrodes are spatially separated by an electrically insulating material, e.g. an upper layer of a passivation stack of the IC.

Preferably, the integrated circuit comprises an interconnect structure over the substrate and at least one passivation layer over the interconnect structure, said gas sensor being at least partially located on the passivation layer. This has the advantage that the gas sensor may be manufactured in the backend of the IC manufacturing process, such that the sensor does not have to be subjected to thermal budgets, e.g. to anneal doping profiles in the substrate, which thermal budgets may damage the sensor.

In a particularly advantageous embodiment, the integrated circuit arrangement further comprises at least one grounding electrode in contact with said volume and a shielding plate in the interconnect structure for shielding the gas sensor from electrical interference, said shielding plate being conductively coupled to the at least one grounding electrode. This protects the gas sensor from electromagnetic radiation emanating from the substrate, e.g. electromagnetic fields generated by circuit elements on the substrate. The at least one grounding electrode may for instance comprise a pair of wires extending alongside said volume.

The excitation electrode and the sensing electrode may be formed by respective wires extending across said volume. This is advantageous because of the relatively large resulting contact area between the electrodes and the volume. Each electrode may be realised by a plurality of parallel wires to further increase contact area. The IC may comprise a pattern of parallel wires in which each wire of the excitation electrode is located adjacent to a wire of the sensing electrode, i.e. an alternating pattern of excitation electrode and sensing electrode wires.

In an embodiment, the volume is delimited by a polymer well structure, said chemical compound being contained in the polymer well structure, said polymer well structure being covered by a gas-permeable membrane. This has the advantage that a liquid volume can be encapsulated in cost-effective and reliable manner on the IC. A particularly suitable material for the polymer well structure is polyimide.

Alternatively, the volume comprises a polymer in which the chemical compound is immobilized, e.g. a sol-gel system or a suitable block co-polymer capable of creating liquid-containing domains. A non-limiting example of such a suitable block co-polymer is a styrene-butadiene-styrene (SBS) block-copolymer such as Kraton®.

The microwave signal may be a signal in the MHz or GHz domain. The microwave signal may further comprise a frequency sweep from a first frequency to a second frequency, e.g. from a low to high frequency or from a high to low frequency, to detect the resonance frequency of the reaction products of the chemical compound and gas in case this resonance frequency is a priori unknown.

The IC arrangement of the present invention may be used to detect the presence of gas in the volume. Preferably, the signal detector is further adapted to determine a gas level in said volume from said phase shift such that the amount of gas in the volume can be quantified.

According to another aspect of the present invention, there is provided a device comprising the integrated circuit arrangement of an embodiment of the present invention. The IC of the present invention may be suitably integrated in devices such as electronic devices, vehicles and so on, as well as in the packaging of packaged items, in which case the IC arrangement may for instance be a RF-ID chip for monitoring environmental conditions of the packaged item, which monitoring data may be relayed to a control centre via the RF link.

In accordance with yet other aspect of the present invention, there is provided a method of detecting a gas using the integrated circuit arrangement of the present invention, the method comprising subjecting the volume to a microwave signal including a resonance frequency of said reaction product; and detecting a change in said microwave signal at said resonance frequency caused by a permittivity change in said volume, said permittivity change being caused by the formation of a reaction product of the chemical compound and the gas in said volume. The step of subjecting the volume to a microwave signal may comprise subjecting the volume to a frequency sweep from a first microwave frequency to a second microwave frequency.

In accordance with yet another aspect of the present invention, there is provided a method of manufacturing an integrated circuit arrangement comprising a gas sensor, comprising providing a substrate covered by an electrically insulating layer, the substrate comprising a signal generator for generating a high frequency signal and a signal detector for detecting a phase shift in the high frequency signal; patterning the electrically insulating layer to form a first trench exposing a conductive contact to the signal generator and a second trench spatially separated from the first trench, said second trench exposing a conductive contact to the signal detector; forming respective electrodes by filling the first trench and a second trench with an electrically conductive material and immobilizing a volume including a chemical compound for reacting with the gas in an acid-base reaction over the respective electrodes.

Preferably, the method further comprises forming an interconnect structure over the substrate; and forming at least one passivation layer over the interconnect structure, said at least one passivation layer including the electrically insulating layer as an upper layer. This has the advantage that the gas sensor is formed in the backend of the IC manufacturing process, as previously explained.

The method may further comprise forming a shielding plate in the interconnect structure, wherein the patterning step further comprises forming a further trench exposing a conductive contact to the shielding plate, and wherein the step of forming the respective electrodes further comprises filling the further trench with an electrically conductive material to form a grounding electrode. This has the advantage that the electrodes of the gas sensor are protected from electromagnetic radiation emanating from the substrate as previously explained.

BRIEF DESCRIPTION OF THE EMBODIMENTS

Embodiments of the invention are described in more detail and by way of non-limiting examples with reference to the accompanying drawings, wherein.

Figure 4:
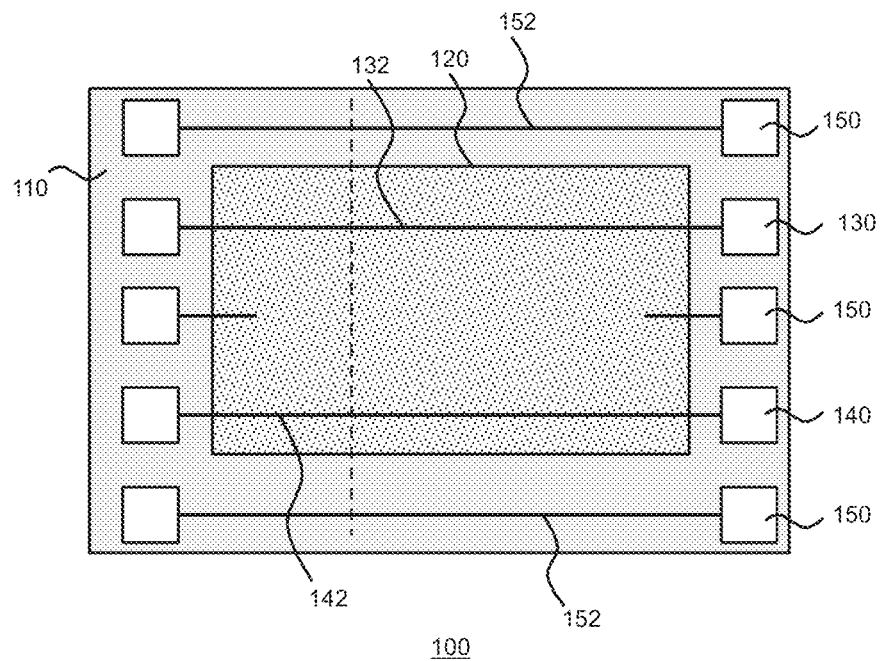
Figure 5:
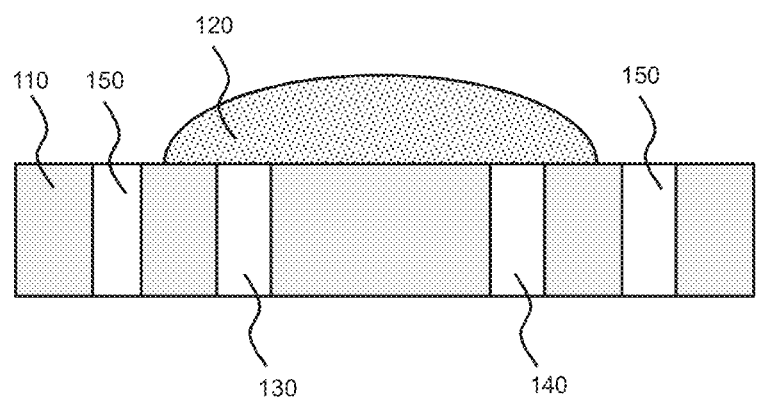
Figure 6:
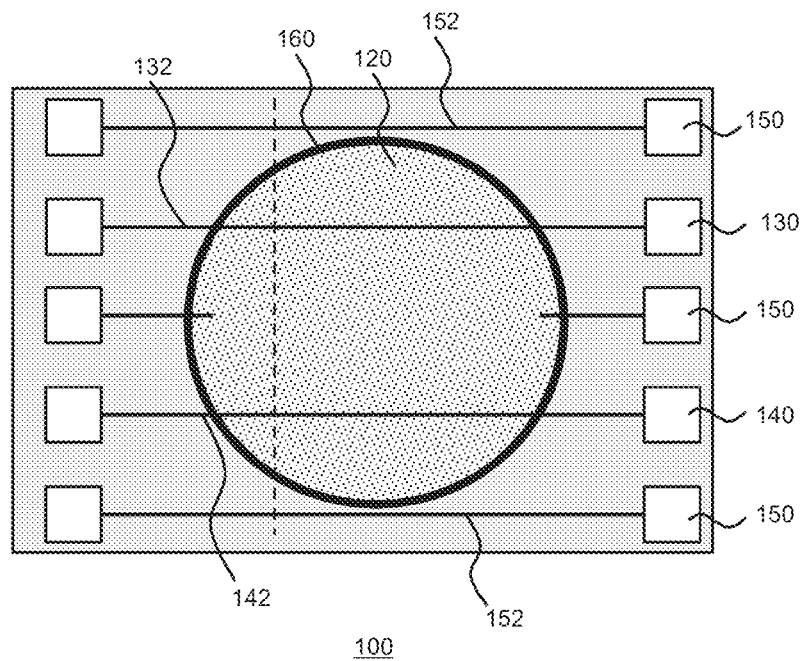
Figure 7:
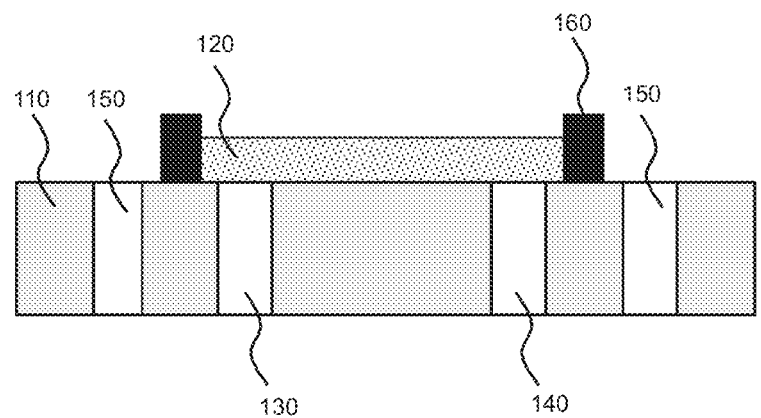
Figure 8:
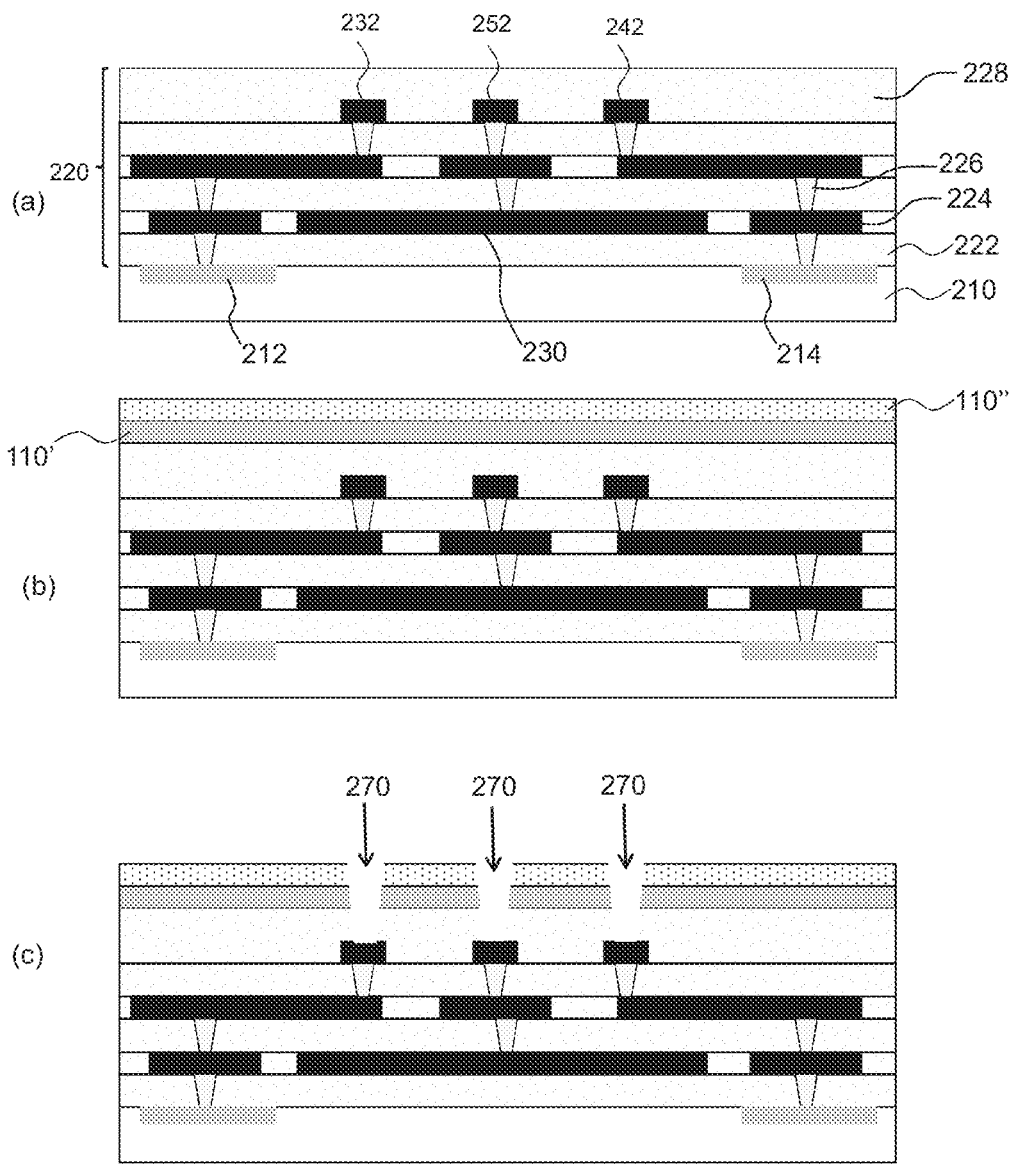
Figure 8:
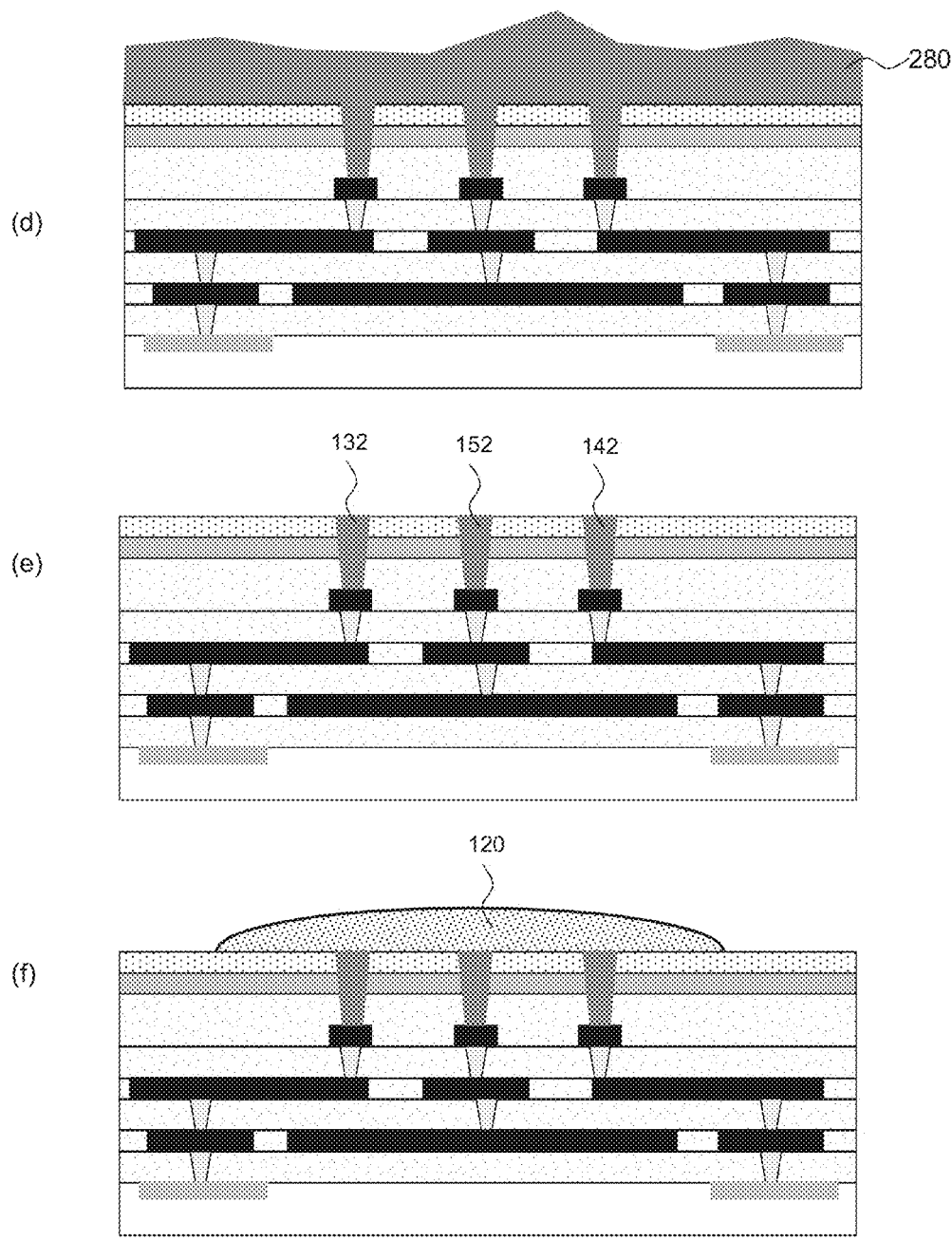

FIG. 4 schematically depicts a top view and FIG. 5 schematically depicts a cross-section across the dashed line in FIG. 4 of an example embodiment of an IC arrangement 100 of the present invention;

FIG. 6 schematically depicts a top view and FIG. 7 schematically depicts a cross-section of another example embodiment of an IC arrangement 100 of the present invention; and FIG. 8 schematically depicts an example embodiment of a method of manufacturing an IC arrangement 100 of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

The present invention utilizes a technique is known as dielectric (relaxation) spectroscopy to determine the presence of ionic species in a sensing volume of a gas sensor, e.g. a $CO_2$ sensor, $SO_2$ sensor, $NH_3$ sensor and so on, that are formed by the acid-base reaction of a chemical compound and the gas. Using such spectroscopy, measurements can be performed at microwave frequencies exceeding the kHz range, e.g. frequencies in the MHz, GHz or even sub-THz domain, as is known per se from studies on the dielectric properties of materials In this technique, microwave stimulation (~GHz) of the materials results in reorientation of permanent electric dipoles that are present, such as non-dissociated ion pairs, asymmetric cations or anions, dissolved water, and so on. Because these dipoles differ in size and strength and interact with different strengths with the surrounding molecules, they display a maximum in this relaxation process at different resonance frequencies. At the resonance frequencies, a maximum in the dielectric loss can be measured.

Basically, the dielectric loss is the imaginary part of the material permittivity as expressed by the Debye equation:

$$\varepsilon(\omega) = \varepsilon_\infty + \frac{(\varepsilon_0 - \varepsilon_\infty)}{(1 + \omega^2 \tau^2)} - i \frac{(\varepsilon_0 - \varepsilon_\infty)}{(1 + \omega^2 \tau^2)} \omega \tau$$

Among the materials already investigated by dielectric relaxation spectroscopy, ionic liquids form a well-studied class of materials. The inventors have realized that such ionic liquids bear a close resemblance with the chemical compounds suitable for reacting with gases such as $CO_2$, such as $CO_2$ sensitive DBU-molecules once these compounds have reacted with $CO_2$.

Figure 1:
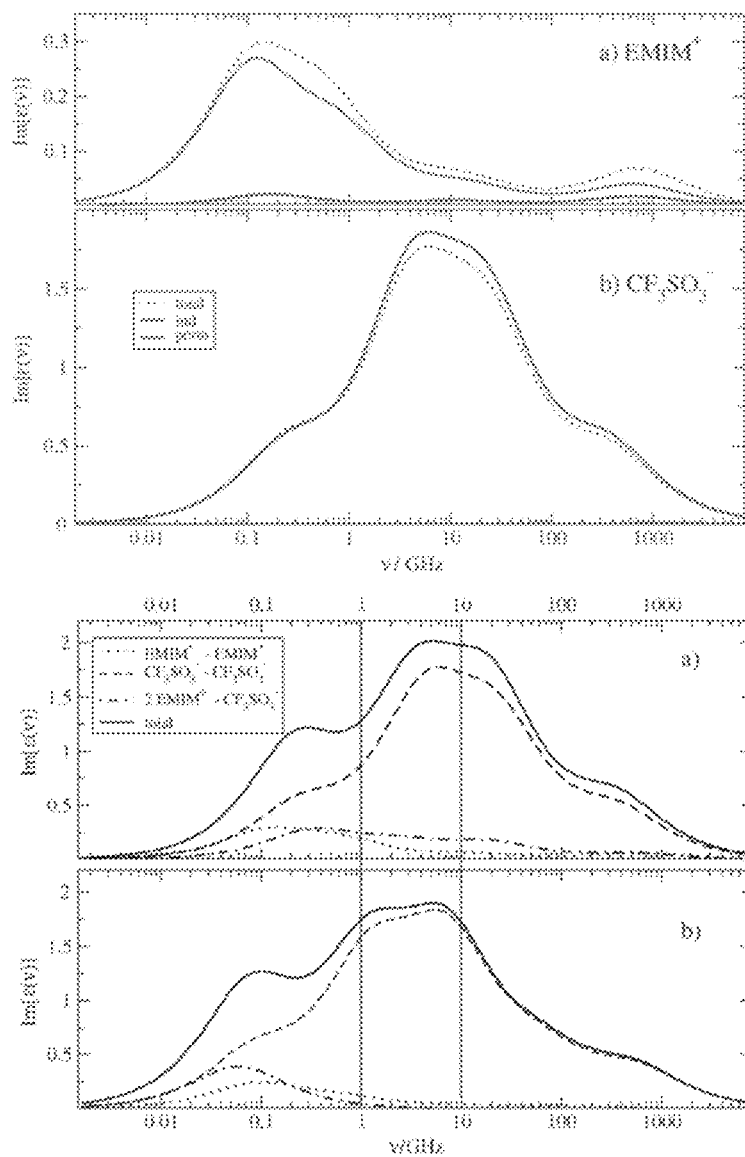
FIG. 1 depicts the dielectric spectrum of the polarizable molecular ionic liquid 1-ethyl-3-methylimidazolium triflate.

As described above, microwave stimulation (~GHz) of the ionic liquids results in reorientation of permanent electric dipoles that are present in the ionic liquid. Moreover using dielectric relaxation spectroscopy, it is possible to discriminate between the different species in the ionic liquid. An example of the distinctive peaks for cations and anions in the ionic liquid is shown in FIG. 1, which shows the dielectric spectrum of the polarizable molecular ionic liquid 1-ethyl-3-methylimidazolium triflate as disclosed by C. Schröder et al. in Phys. Chem. Chem. Phys., 13, p. 12240-12248 (2011). Because the ethyl-3-methylimidazolium cation [Emim$^+$] interacts differently with its surroundings and has a different magnitude/amplitude than the dipole of the triflate anion [Tf$^-$], it displays a different maximum loss frequency as indicated by the height and position of these signals.

Figure 2:
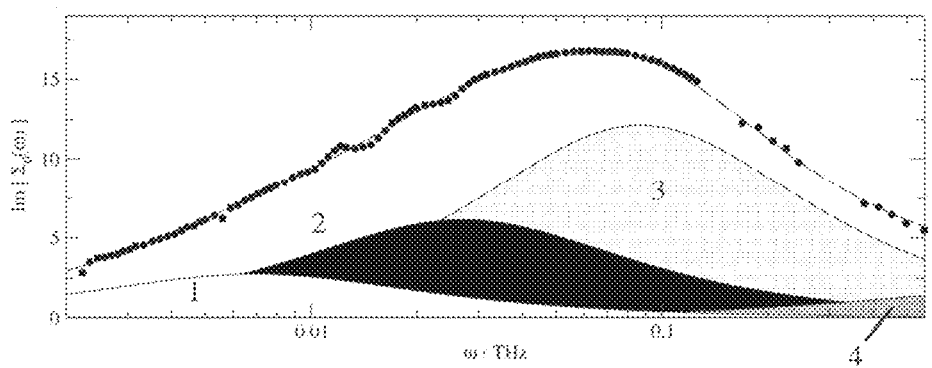
FIG. 2 shows the dielectric spectra of mixtures of the ionic liquid 1-butyl-3-methyl-imidazolium (BMIM(+)) tetrafluoroborate ($BF_4^-$) with water (water mole fraction=0.9) at three selected mole fractions.

Additionally, FIG. 2 shows the dielectric spectra of mixtures of the ionic liquid 1-butyl-3-methyl-imidazolium (BMIM(+)) tetrafluoroborate ($BF_4^-$) with water (water mole fraction=0.9) at three selected mole fractions, as disclosed by C. Schröder et al. in J. Chem. Phys., 129, page 184501 (2008). In FIG. 2, signals 1 and 2 originate from the ionic liquid dipole relaxation, whereas signals 3 and 4 orginate from the water dipole relaxation. This graph clearly demonstrates that despite the high amount of water in the mixture, the contribution from the ionic liquid is clearly distinguishable; dielectric loss in the MHz to low GHz region originates from the ionic liquid, while the $H_2O$ dipole relaxation occurs in the medium to high GHz region.

Figure 3:
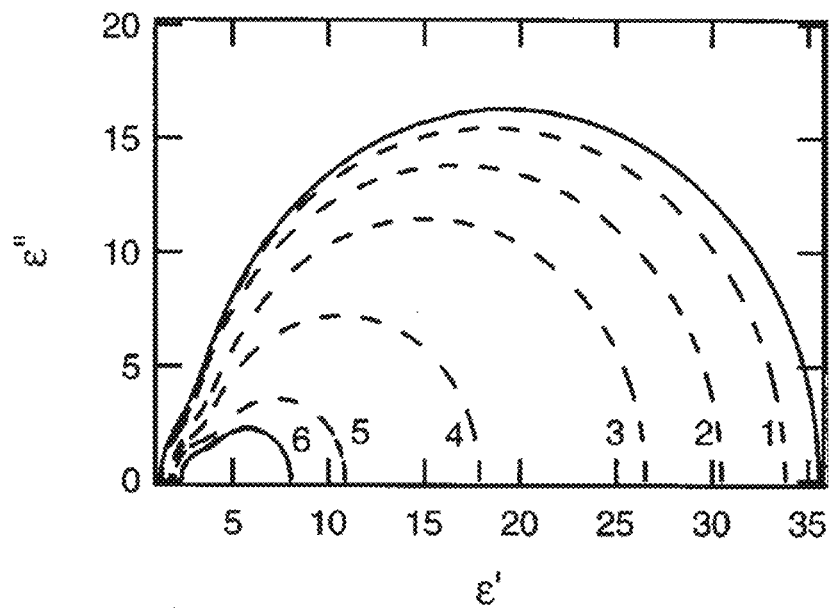
FIG. 3 depicts a Cole-Cole diagram showing the change in the real part ($\in'$) and imaginary part ($\in''$) of the permittivity while increasing the concentration of [Emim$^+$][Tf$^-$] in acetonitrile.

The shape of the dielectric loss signal, namely the peak height and to a lesser extent its position, may also depend on the amount of dipoles in an inert medium. An example demonstration of this effect is shown in FIG. 3, which depicts a Cole-Cole diagram showing the change in the real part ($\in'$) and imaginary part ($\in''$) of the permittivity while increasing the concentration of [Emim$^+$][Tf$^-$] in acetonitrile, with 1 being pure acetonitrile and 6 being pure [Emim$^+$][Tf$^-$], as disclosed by M. L. T. Asaki et al. in J. Chem. Phys., 116 (23), p. 10377-10385 (2002).

This principle may be applied to the detection of the ion pair formed in the acid-base reaction between a chemical compound and a gas of interest, such as by way of non-limiting example the nitrogen-containing cation and the $CO_2$-containing anion in a sensing volume comprising an chemical compound including for instance a diamine amidine, guanidine, mono- or di-silyl amine functional group and so on for reacting with $CO_2$. For example, in the case of DBU as the base reacting with (acidic) $CO_2$, it is necessary to distinguish between signals originating from $DBUH^+$ and $RCO_3^-$ on the one hand and water+other compounds of the 3-component system on the other hand. Knowing the material properties of the 3-component system (e.g., viscosities, average molecular diameter and so on), the expectation values of the resonance frequencies are located in the range from 0.5 to 20 GHz. Such expectation values can be calculated using the Stokes-Einstein equation, and more particularly using the electrical mobility equation.

In short, the present invention is based on the insight that high-frequency or microwave impedance measurements in the MHz, GHz or even sub-THz domain can be used to determine the dielectric loss peak due to dipole reorientations, which has the additional advantage that the cross-sensitivity of the measurements to water is reduced as the signals attributable to the presence of water are separated from the signals relating to the ionic species of interest.

FIG. 4 schematically depicts a top view and FIG. 5 schematically depicts a cross-section across the dashed line in FIG. 4 of an example embodiment of an IC arrangement 100 of the present invention, which includes a gas sensor utilizing the aforementioned dielectric loss measurement principle. The gas sensor comprises a plurality of electrodes 132, 142 and optional electrodes 152 formed in a dielectric layer 110.

A volume 120 comprising a polymer matrix encapsulating the chemical compound that reacts with the gas of interest in an acid-base reaction, e.g. forms a zwitterionic pair, over the excitation electrode 132 and the sensing electrode 142 such that these electrodes are in conductive contact with the volume 120. Any suitable chemical compound may be used for this purpose, e.g. DBU or any other compound that can form such a zwitterionic reaction product when reacting with gas as previously explained.

The electrode 132, which may optionally be connected to contact pads or bond pads 130, is an excitation electrode for exposing the volume 120 to a high-frequency (microwave) alternating current. The one or more frequencies of the alternating current typically lie in the MHz, GHz or sub-THz range. The electrode 142, which may optionally be connected to contact pads or bond pads 140, is a sensing electrode for sensing the dielectric loss in the volume 120 upon its exposure to the high-frequency alternating current.

The excitation electrode 132 and the sensing electrode 142 are respectively conductively or capacitively coupled to a signal generator (not shown) and a signal detector (not shown), which may be different circuits or may be different functionalities of a single circuit, e.g. a signal processor. In an embodiment, the signal detector is adapted to detect changes to the imaginary part ($\in''$) of the permittivity of the volume 120, i.e. dielectric loss in the volume 120. In an alternative embodiment, the signal detector is adapted to detect changes to the real part ($\in'$) of the permittivity of the volume 120, i.e. loss of capacitance in the volume 120. Both embodiments utilize the fact that the real and imaginary parts of the Debye equation are dependent on the resonance frequency of the associated dipoles in the volume 120.

In an embodiment, the signal generator is adapted to provide the excitation electrode 132 with a high-frequency sweep, i.e. a frequency scan from a first value to a second value in the appropriate frequency domain. This is for instance advantageous when the actual resonance frequency of the ion pair of interest, i.e. the zwitterion pair formed in the acid-base reaction, is unknown, such that the first and second values of the frequency sweep define a frequency window within the resonance frequencies of the ion pair of interest are likely to reside. It is relatively straightforward to identify the resonance signals belonging to the ion pair of interest as these signals tend to occur at a lower frequency than e.g. water signals due to the larger size of the ion pair of interest.

In an alternative embodiment, the signal generator is adapted to provide the excitation electrode 132 with one or more alternating current signals of a discrete frequency, which for instance is advantageous when the resonance frequencies of the ion pair of interest are known a priori, in which case the one or more discrete frequency signals provided by the signal generator coincide with the one or more resonance frequencies of the ion pair of interest.

In the context of the present application, the IC arrangement 100 may comprise a single IC, in which case the signal generator and the signal detector are located on the IC, or may comprise a separate device including the signal generator and the signal detector, in which case the excitation electrode 132 and the sensing electrode 142 may be permanently or temporarily connected to the signal generator and the signal detector respectively via optional bond pads 130, 140.

In an embodiment, the gas sensor of the IC arrangement 100 may further comprise one or more grounding electrodes 152, which may be connected to optional bond pads 150. The grounding electrodes 152 are connected to a grounding structure such as a field plate or shielding plate (not shown) underneath the excitation electrode 132 and the sensing electrode 142, i.e. in between these electrodes and the substrate (not shown) to protect the excitation electrode 132 and the sensing electrode 142 from electromagnetic interference emanating from the substrate, e.g. by switching behaviour of switches, e.g. transistors, on the substrate, as will be explained in more detail below.

The chemical compound may be immobilized in the volume 120 in any suitable manner. For instance, the chemical compound, either in neat form or dissolved in a suitable solvent, e.g. an alcohol having negligible vapour pressure at room temperature (25° C.), such as oleyl alcohol, may be encapsulated in a polymer matrix, which may be formed by a curing reaction (chemically cross-linked polymers) or by self-assembly (physically cross-linked polymers).

An alternative embodiment of immobilizing the chemical compound is shown in FIGS. 6 and 7, which respectively depict a top-view and a cross-section of another embodiment of the IC 100 of the present invention, in which the chemical compound is placed inside a limiting structure 160 such as a polymer well structure formed on top of the passivation or metallization stack of the IC. Such a well structure 160 may for instance comprise a polyimide well structure comprising an inner well in which the chemical compound is placed and an outer well (not shown) in which a $CO_2$-permeable membrane covering the inner well is anchored. Such well structures and membranes are well known per se in the art, e.g. from the field of bodily fluid sensors. For instance, an example of a gas sensor utilizing such a well structure is disclosed in U.S. Pat. No. 5,376,255. An advantage of this embodiment is that the chemical compound may be placed inside the inner well in liquid form, e.g. neat or dissolved in a suitable solvent, such that no separate immobilization steps are required.

An example embodiment of the manufacture of a gas sensor in the backend of an IC manufacturing process, i.e. on top of the metallization, is shown in FIG. 8. It should be understood that this process flow is just one of many possible approaches that may be chosen for such a manufacturing process and that may alternatives, e.g. the interchange or omission of selected process steps will be apparent to the skilled person.

The method commences in step (a) with the provision of a semiconductor substrate 210 carrying a plurality of circuit elements, e.g. transistors, diodes and so on, with part of the circuit elements defining a signal generator 212 and a signal detector 214 respectively. A metallization stack 220 is formed on the substrate 210 comprising at least one patterned metal layer 224 and an electrically insulating layer 222 is formed. Any suitable number of metal layers 222 and dielectric layers 224 may be present. The upper metal layer may comprise any suitable number of bond pads as well as metal portions 232, 242 and optionally 252 for conductively coupling the appropriate circuit elements 212, 214 to the electrodes 132 and 142 in case of a $CO_2$ sensor 120 being operated by circuit elements 212, 214 of the IC 100.

Metal portions in different patterned metal layers 224 may be conductively interconnected by one or more vias 226 formed in a dielectric layer 222 in between the respective portions of the patterned metal layers 224. Any suitable material may be used to form the metallization stack, such as Ti, TiN, Al, Cu and combinations thereof to define the metal layers 224 and silicon oxide, silicon nitride, low-k dielectrics and other dielectric materials as well as combinations thereof to form the dielectric layers 222. Although in FIG. 8(a) these layers are depicted as single layers, it should be understood that these layers themselves may comprise a stack of layers, as is common design practice in contemporary semiconductor technologies such as sub-micron CMOS technologies.

Optionally, the metallization stack 220 may comprise a shielding plate 230 in one of the metal layers 224, which may be connected to ground (not shown) and which may provide protection for the $CO_2$ sensor against electromagnetic interference from the circuit elements on the substrate 210. In case of the presence of shielding plate 230 the metallization stack 220 further comprises at least one metal portion 252 conductively connected to the shielding plate 230.

A passivation stack comprising one or more dielectric layers 110', 110" is formed over the metallization stack. In FIG. 8(b), the passivation stack comprises a silicon nitride layer 110' and a silicon oxide layer 110" by way of non-limiting example only. Such layers may be formed in any suitable manner to any suitable thickness. By way of non-limiting example only, the silicon nitride layer 110' may be formed in a plasma-enhanced chemical vapour deposition (PE-CVD) step to a thickness of approximately 600 nm and the silicon oxide layer 110" may be formed to a thickness of approximately 100 nm using a high-density plasma oxidation step in a 140 nm CMOS process. In an embodiment, the deposition of the silicon oxide layer 110" may also be used to form an upper dielectric layer 228 over the upper metallization layer of the metallization stack.

A planarization step such as a chemical mechanical polishing (CMP) step may be applied to planarize the silicon nitride layer 110' if necessary. This is not shown for the sake of brevity only. It will be obvious to the skilled person that different layer thicknesses and different materials may be used for the planarization stack depending on process technology and requirements. For instance, the silicon nitride layer 110' may be a silicon-rich SiN layer, as this material has a good selectivity towards HF vapour-based etch recipes and resists polymer formation during such an etching step.

In step (c), trenches 270 are formed through the passivation stack layers 110' and 110" using one or more suitable etch recipes to provide access to the electrode contacts 232, 242 and optionally 252 in the upper metallization layer 224. A suitable diameter of the trenches 270 in a 140 nm CMOS process is 700 nm although different dimensions will obviously be appropriate for different scale technologies. The trenches 270 may be defined using any suitable mask, e.g. a hard mask or a photolithographic mask, as is well known per se to the skilled person.

Next, the trenches 270 are filled with a conductive material 280, e.g. tungsten, using any suitable deposition process such as chemical vapour deposition (CVD) in step (d), to form electrodes 132, 142 and optionally 152 through the passivation stack defined by dielectric layers 110' and 110", and in step (e) excess conductive material 280 is removed, e.g. by applying a planarization step, e.g. a CMP step, terminating on the upper passivation layer 110".

Next, in step (f) a volume 120, e.g. one or more droplets, of a composition including a volatile solvent and the chemical compound for forming a reaction product with the gas of interest in an acid-base reaction dissolved in said volatile solvent together with a precursor of a polymer matrix, e.g. a dissolved polymer or polymer precursor, is deposited on at least the electrodes 132 and 142, e.g. using pipetting or inkjet printing by for instance a micro-drop printer, after which the volatile solvent is evaporated from the composition to form the polymer matrix that traps the chemical compound over at least the electrodes 132 and 142. The polymer matrix may for instance be formed by chemical crosslinking, e.g. curing a suitable monomer in the composition 180, such as by the photo-induced hydrolysis of a siloxane to form a polysiloxane such as PDMS.

Alternatively, the polymer matrix is formed by physical gelation or crosslinking, e.g. using a hydrophobic polymer gel or a non-crystalline wax, or by aggregation of a block copolymer that has been dissolved in the composition 180, the latter being particularly advantageous as it does not require chemical reactions to form the polymer matrix, thus reducing the risk that the chemical composition or structure of the chemical compound is negatively affected during the formation of the polymer matrix. The IC 100 may subsequently be finalized using any suitable processing steps.

As previously mentioned, particularly suitable materials for forming the polymer matrix are polymers that aggregate or gelate according to a mechanism sometimes referred to as physical crosslinking, thereby forming multiple domains, in particular a first domain of relatively high structural rigidity, which defines the boundaries or walls of a second domain in which materials can be encapsulated. Polymers that are known to exhibit such properties include polymers comprising two or more blocks of different polymers or oligomers. Such polymers will be referred to as block copolymers in the present application. The different blocks of the copolymers are typically selected to respectively provide the aforementioned first and second domains.

In an embodiment, the polymer used to form the polymer matrix is a polymer according to general formula [A][B], wherein A is a hard polymer and B is a soft polymer, and wherein A is selected from polystyrenes, polyacrylates, polycarbonates and combinations thereof, and B comprises one or more linear or branched polyalkanes, e.g. rubber blocks, polyalkenes, polyesters or polyethers, e.g. polyethyleneglycol or polytetrahydrofuran. The A blocks are suitable polymers for the formation of the first domains due to their relatively rigid structure, wherein the B blocks are suitable polymers for the formation of the second domains due to their relatively flexible structure.

Polystyrene is particularly suitable as an embodiment of the A block, whereas rubber blocks are particularly suitable as an embodiment of the B block. It is for instance known that styrene-butadiene-styrene (SBS) block co-polymers are capable of physical crosslinking, i.e. of gel formation without requiring chemical reaction.

However, step (f) may be replaced by a three-step process in which a polymer, e.g. polyimide, well structure is formed on the upper planarization layer 110", which is subsequently filled with the chemical compound to form the volume 120, either in neat form or dissolved in a suitable solvent, after which a gas-permeable membrane such as a $CO_2$-permeable membrane is formed over the well structure to trap the chemical compound inside the well structure. This embodiment has the advantage that a curing step can be avoided, thus avoiding the risk of the acid or base functionality of the chemical compound reacting with the polymer matrix, and ensures a secure entrapment of the chemical compound on the IC 100, which is less sensitive to slow evaporation of the chemical compound from the volume 120.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit arrangement comprising:
   a substrate; and
   a gas sensor comprising:
   at least a pair of spatially separated electrodes including an excitation electrode and a sensing electrode;
   a volume in contact with said pair of electrodes, said volume including a chemical compound for forming a reaction product with said gas in an acid-base reaction;
   a signal generator conductively or capacitively coupled to the excitation electrode and adapted to provide the excitation electrode with a microwave signal including a resonance frequency of said reaction product;
   a signal detector conductively or capacitively coupled to the sensing electrode and adapted to detect a change in said microwave signal at said resonance frequency caused by a permittivity change in said volume, said permittivity change being caused by the presence of said reaction product; and
   wherein the excitation electrode and the sensing electrode are formed by respective wires extending across said volume.

2. The integrated circuit arrangement of claim 1, wherein the electrodes are spatially separated by an electrically insulating material.

3. The integrated circuit arrangement of claim 1, wherein the integrated circuit arrangement comprises an interconnect structure over the substrate and at least one passivation layer over the interconnect structure, said gas sensor being at least partially located on the passivation layer.

4. The integrated circuit arrangement of claim 3, further comprising at least one grounding electrode in contact with said volume and a shielding plate in the interconnect structure for shielding the gas sensor from electrical interference, said shielding plate being conductively coupled to the at least one grounding electrode.

5. The integrated circuit arrangement of claim 4, wherein the at least one grounding electrode comprises a pair of wires extending alongside said volume.

6. The integrated circuit arrangement of claim 1, wherein the volume is delimited by a polymer well structure, said chemical compound being contained in the polymer well structure, said polymer well structure being covered by a gas-permeable membrane.

7. The integrated circuit arrangement of claim 6, wherein the polymer well structure comprises polyimide.

8. The integrated circuit arrangement of claim 1, wherein the volume comprises a polymer in which the chemical compound is immobilized.

9. The integrated circuit arrangement of claim 1, wherein the microwave signal comprises a frequency sweep from a first frequency to a second frequency.

10. The integrated circuit arrangement of claim 1, wherein the signal detector is further adapted to derive a gas concentration in said volume from said change in the high frequency signal.

11. The integrated circuit arrangement of claim 1, wherein the gas sensor is a $CO_2$ sensor, and wherein the chemical compound has a functional group such as a diamine, amidine, mono-silyl amine, di-silyl amine or guanidine functional group.

12. A device comprising the integrated circuit arrangement of claim 1.

13. A method of measuring a gas concentration using the integrated circuit arrangement of claim 1, the method comprising:
   subjecting the volume to a microwave signal including a resonance frequency of said reaction product; and
   detecting a change in said microwave signal at said resonance frequency caused by a permittivity change in said volume, said permittivity change being caused by the formation of a reaction product of the chemical compound and the gas in said volume.

14. The method of claim 13, wherein the step of subjecting the volume to a microwave signal comprises subjecting the volume to a frequency sweep from a first microwave frequency to a second microwave frequency.

* * * * *